(12) United States Patent
Eblen, Jr. et al.

(10) Patent No.: US 6,734,975 B1
(45) Date of Patent: May 11, 2004

(54) HYDROGEN CONTAMINATION MONITORING AND SENSOR EVALUATION SYSTEM

(75) Inventors: John P. Eblen, Jr., Newbury Park, CA (US); Jeffrey H. Hunt, Chatsworth, CA (US); Albert D. Tomassian, West Hills, CA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 10/304,470

(22) Filed: Nov. 26, 2002

(51) Int. Cl.$^7$ .............................................. G01N 21/55
(52) U.S. Cl. ...................... 356/445; 356/448
(58) Field of Search ................... 356/445–448

(56) References Cited

U.S. PATENT DOCUMENTS

| | | | | |
|---|---|---|---|---|
| 5,404,218 A | * | 4/1995 | Nave et al. ................ | 356/301 |
| 6,160,278 A | * | 12/2000 | Liu et al. ..................... | 257/252 |
| 6,519,041 B1 | * | 2/2003 | Berthold ..................... | 356/477 |
| 2002/0171839 A1 | * | 11/2002 | DiMeo et al. .............. | 356/437 |

OTHER PUBLICATIONS

H. W. K. Tom, Second–Harmonic Reflection from Silicon Surfaces and its Relation to Structural Symmetry, Nov. 21, 1983, Physical Review Letters.*
T. F. Heinz, Study of Si(111) Surfaces by OPtical Second–Harmonic Generation: Reconstruction and Surface Phase Transformation, Jan. 7, 1985, Physical Review Letters.*
X. D. Zhu, Surface Diffusion of CO on Ni(111) Studied by Diffraction of Optical Second–Harmonic Generation off a Monolayer Grafting, Dec. 19, 1988, Physical Review Letters.*

* cited by examiner

Primary Examiner—Michael P. Stafira
(74) Attorney, Agent, or Firm—William C. Anderson

(57) ABSTRACT

A hidrogen detection system (14) includes a hydrogen sensor(16) that detects contamination within a reaction member and generates a hydrogen contamination signal. A surface spectroscopic system (18) is operational in conjuction with the hydrogen sensor (16) and determines contamination of the hydrogen sensor (16) and generates a sensor contamination signal. A controller (20) is electrically coupled to the hydrogen sensor (16) and the surface spectroscopic system (18) and compares the hydrogen contamination signal to the sensor contamination signal and generates a corrected hydrogen contamination signal.

20 Claims, 2 Drawing Sheets

HYDROGEN CONTAMINATION MONITORING AND SENSOR EVALUATION SYSTEM

RELATED APPLICATION

The present invention is related to U.S. Pat. No. 5,623,341 entitled "Method of monitoring a surface using surface spectroscopy", which is incorporated by reference herein.

TECHNICAL FIELD

The present invention relates generally to hydrogen leak detection systems and surface spectroscopic processes, and more particularly, to a system and method of detecting and monitoring hydrogen contamination of palladium surfaces and utilizing information contained therein for hydrogen sensor evaluation.

BACKGROUND OF THE INVENTION

Detecting leakage of gaseous hydrogen (GH2) in hydrogen-fueled vehicles is critical in preventing generation or accumulation of flammable and explosive concentrations. Concentrations of GH2 that are greater than or equal to approximately 4% in air are flammable and can be explosive. GH2 leakage detection is also desired for emerging hydrogen fuel-celled infrastructures.

In hydrogen-fueled launch vehicles, during cryogenic storage and subsequent transport of liquid hydrogen, leaks typically occur and are associated with sealed connections. To detect the leaks mass spectrometers are typically utilized. Mass spectrometers have sufficient chemical specificity detection capability to allow detection of leaking amounts of GH2 as opposed to detection of other atmospheric contaminants, such as carbon disulfide, carbon monoxide, and methane that exist in an operating environment.

However, mass spectrometers have unacceptably slow response time in detection of leaking GH2 when applied to large vehicles, such as rockets and the like. Palladium based sensors, on the other hand, have a relatively quick response time in detection of GH2. Multiple palladium sensors are based on reversible changes in the physical properties of palladium in the presence of GH2 or are based on use of palladium as a catalyst for reversible chemical reactions in detection of GH2.

Unfortunately, palladium sensors lack the chemical specificity capability required for deciphering between GH2 and other atmospheric contaminants. Also, the palladium sensors, due to being chemically affected or "poisoned" by multiple contaminants, have a limited service life. It can be difficult to determine when the service life is up and when a palladium sensor needs to be repaired or replaced.

A couple of techniques have been suggested to overcome the disadvantages associated with palladium sensors. One technique is the use of thin films over surfaces of the palladium sensors that only allow passage of GH2 as opposed to the other atmospheric contaminants. The use of thin films although preventing clogging of the palladium surfaces increases complexity of a sensor system, reduces GH2 detection response time, and causes a sensor to become application specific.

Another technique is to heat resistive portions of the palladium sensors to desorb contaminants and extend service life of the sensors. In heating the sensors, temperature changes are monitored to detect amounts of GH2. Temperature changes are different for GH2 contamination versus other contamination. In order to heat the, resistive portions system and operational complexity is increased. Additionally, there is a significant amount of ambiguity in monitoring the temperature changes, which can cause incorrect GH2 contamination determination.

It is therefore desirable to provide a GH2 contamination detection system that has sufficient chemical specificity capability, has a relatively quick GH2 detection response time, and is capable of determining when a sensor is operating inappropriately and needs to be repaired, recalibrated, or replaced.

SUMMARY OF THE INVENTION

The present invention provides a system and method of detecting and monitoring hydrogen contamination of palladium surfaces and utilizing information contained therein for hydrogen sensor evaluation. A hydrogen detection system is provided and includes a hydrogen sensor that detects contamination within a reaction member and generates a hydrogen contamination signal. A surface spectroscopic system is operational in conjunction with the hydrogen sensor and determines contamination of the hydrogen sensor and generates a sensor contamination signal. A controller is electrically coupled to the hydrogen sensor and the surface spectroscopic system and compares the hydrogen contamination signal to the sensor contamination signal and generates a corrected hydrogen contamination signal.

The present invention has several advantages over existing hydrogen detection sensors. One advantage is that it provides accurate chemical specificity capability and at the same time provides relatively quick GH2 detection response time.

Another advantage of the present invention is that it provides a system for evaluating performance of a hydrogen sensor so as to determine when to repair, recalibrate, or replace the hydrogen sensor.

Furthermore, the present invention provides a hydrogen detection and evaluation system that is not application specific in that it is easily configured for multiple applications.

The present invention itself, together with further objects and attendant advantages, will be best understood by reference to the following detailed description, taken in conjunction with the accompanying drawing.

DETAILED DESCRIPTION OF THE PREFERRED EMBODIMENT

Figure 1A:
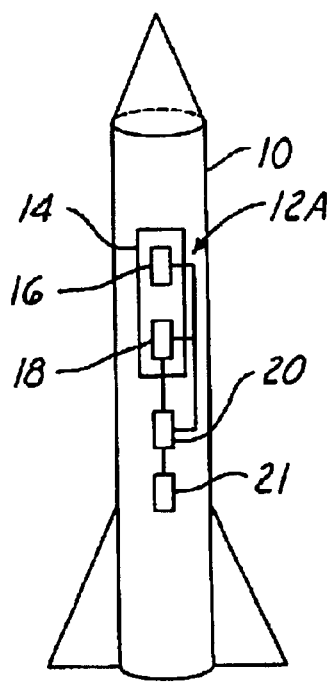
FIG. 1A is a perspective view of a hydrogen-fueled vehicle utilizing a hydrogen detection and sensor evaluation system having internal control in accordance with an embodiment of the present invention.

In each of the following figures, the same reference numerals are used to refer to the same components. While the present invention is described with respect to a system and method of detecting and monitoring hydrogen contamination of palladium surfaces and utilizing information contained therein for hydrogen sensor evaluation, the present invention may be adapted for various applications including automotive, marine, aerospace, and other applications known in the art. The present invention may be applied to hydrogen fueled vehicles, such as a rockets, to hydrogen fuel-cell vehicles, or to other applications requiring detection of hydrogen.

In the following description, various operating parameters and components are described for one constructed embodiment. These specific parameters and components are included as examples and are not meant to be limiting.

Also, in the following description the term "resonant frequency" refers to a frequency at which a vibration exists at that frequency having a large amplitude that was caused by a relatively small stimulus of approximately the same frequency. A hydrogen sensor may have a palladium surface that is contaminated with one or more elements. The surface may have multiple resonating frequencies, depending upon chemical make-up and contamination of the surface. Each resonating frequency may correspond to a particular chemical element or chemical compound at which an impeding signal or a harmonic of the impeding signal transmitted at a particular resonating frequency significantly increases in amplitude upon reflecting off the surface and thus identifying that element or chemical compound. For example, a palladium surface contaminated with hydrogen may have a resonating frequency for hydrogen alone or for various compound combinations of hydrogen and palladium. A frequency may be "on" resonance, meaning the frequency is or has a harmonic that is approximately the same as a resonating frequency, or "off" resonance, where the frequency or harmonics thereof are frequencies other than the resonating frequency.

Figure 1B:
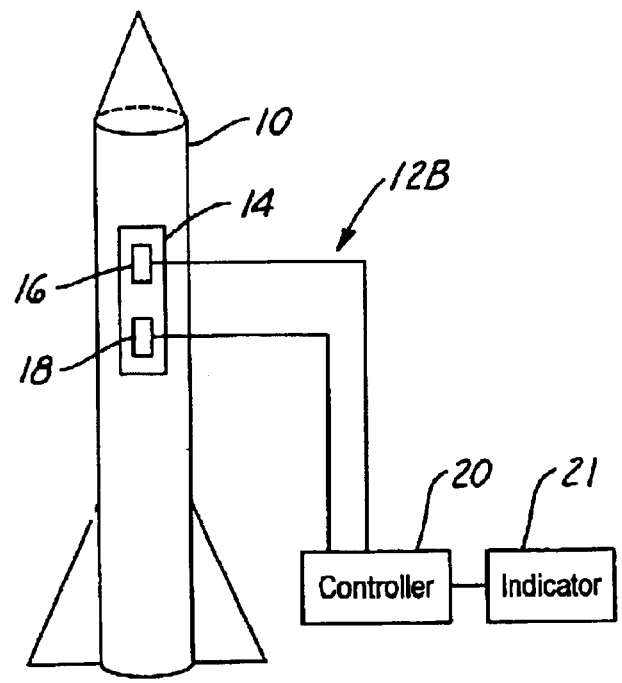
FIG. 1B is a perspective view of a hydrogen-fueled vehicle utilizing a hydrogen detection and sensor evaluation system having external control in accordance with an embodiment of the present invention.

Referring now to FIGS. 1A and 1B, perspective views of hydrogen-fueled vehicles 10 utilizing hydrogen detection and sensor evaluation systems 12A and 12B having internal control and external control, respectively, are shown in accordance with an embodiment of the present invention. Each hydrogen detection and sensor evaluation system 12A and 12B includes a hydrogen detection system 14 having at least one hydrogen detection sensor 16 and at least one surface spectroscopic system 18. The hydrogen detection sensors 16 are used to detect hydrogen leaks in the hydrogen-fueled vehicles 10. The surface spectroscopic systems 18 are used in determining species identity and contamination levels of the hydrogen detection sensors 16 as well as for sensor performance evaluation. A controller 20 is coupled to the hydrogen sensors 16 and the surface spectroscopic systems 18 and is used in determining actual contamination of the hydrogen sensors 16 and in sensor evaluation. The controller 20 indicates performance of the sensor 16 via an indicator 21.

The controller 20 may be incorporated internal to a vehicle, as shown in FIG. 1A, or may be external to a vehicle and used in detecting hydrogen leaks before launch of the vehicle, as shown in FIG. 1B. The controller 20 is preferably microprocessor based such as a computer having a central processing unit, memory (RAM and/or ROM), and associated input and output buses. The controller 20 may be a portion of a central main control unit, incorporated in a surface spectroscopic system, or may be a stand-alone controller as shown.

The indicator 21 may be of various type and style known in the art. The indicator 21 may be as simple as a light emitting diode (LED) or set of LEDs or may be as complicated as a monitor illustrating various sensor performance characteristics known in the art.

Figure 2:
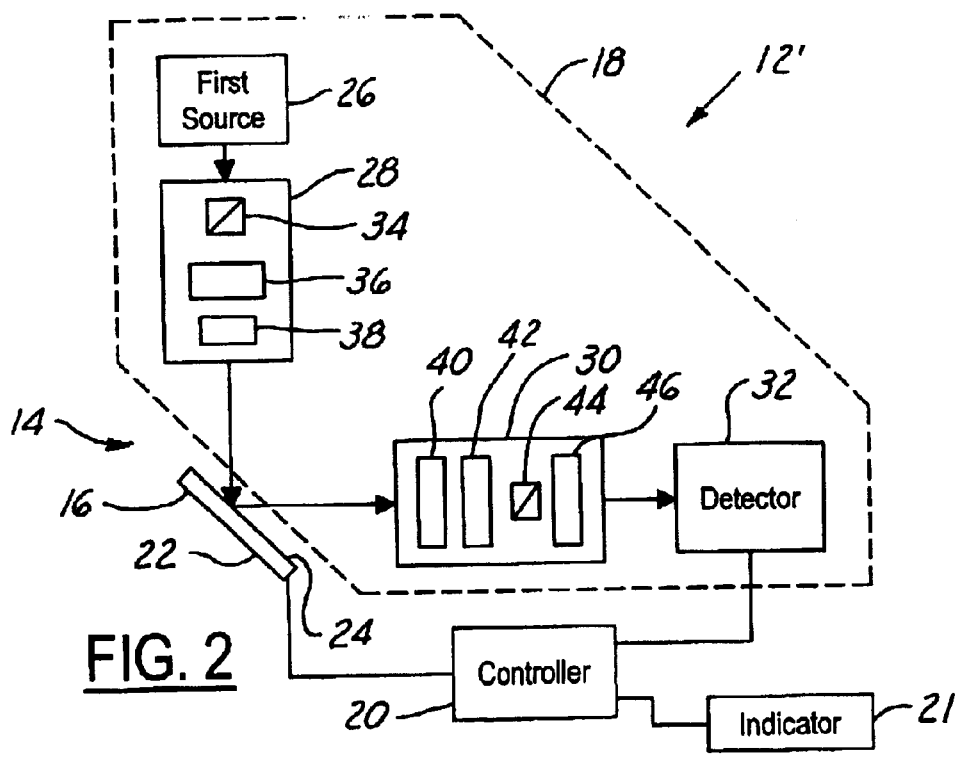
FIG. 2 is a block diagrammatic view of a hydrogen detection and sensor evaluation system in accordance with an embodiment of the present invention.

Referring now to FIG. 2, a block diagrammatic view of a hydrogen detection, and sensor evaluation system 12' in accordance with an embodiment of the present invention is shown. The detection and evaluation system 12' includes the hydrogen detection sensor 16, the surface spectroscopic system 18, and the controller 20.

The hydrogen detection sensor 16 has a reaction member 22 with an impact surface 24. The reaction member 22 although may be formed of various materials is preferably formed at least partially with palladium. Palladium, as known in the art, has a relatively quick response in detection of hydrogen. The hydrogen detection sensor 16 may be resistive in nature in that it changes in resistance with change in contamination level. The hydrogen detection sensor 16 may be of various size, shape, style, and may be used in various locations on the vehicle 10.

The surface spectroscopic system 18 includes a first source 26, a first input device 28, an output device 30, and a detector 32. The surface spectroscopic system for example may be a SURFace Spectroscopy (SURFS) diagnostics system by The Boeing Company or other surface spectroscopy system known in the art. Although, the first source 26 is preferably a light source generating and transmitting signals containing electromagnetic radiation, such as a laser, it may be some other type of source known in the art.

The first input device 28 includes an amplitude adjuster 34, a polarizer 36, and a frequency adjuster 38. The amplitude adjuster 34 adjusts amplitude of the transmitted signals. The polarizer 36 is used in adjusting polarization characteristics of the signals. The frequency adjuster 38 is used in selecting one or more desired transmitted frequency components and removing other frequency components of the transmitted signals. The amplitude adjuster 34, the polarizer 36, and the frequency adjuster 38 may be formed of optics and include various filters such as color filters and frequency filters. The input device 28 directs the transmitted signals at desired frequencies to impede upon and reflect from the impact surface 24 to form reflected signals.

The output device 30 includes a frequency selector 40, an output amplitude adjuster 42, an output polarizer 44, and may include other signal conditioning devices as known in the art and designated by box 46. The output device 30 is used in selecting reflected signals having desired frequencies. As with the input device 28 the output device 30 may also be formed of various optics and filtering devices.

The detector 32 performs as an optical to electronic signal converter. In one embodiment of the present invention, the detector 32 receives the reflected signals in the form of an electromagnetic radiation and generates an electronic signal representation of the reflected signals.

Figure 3:
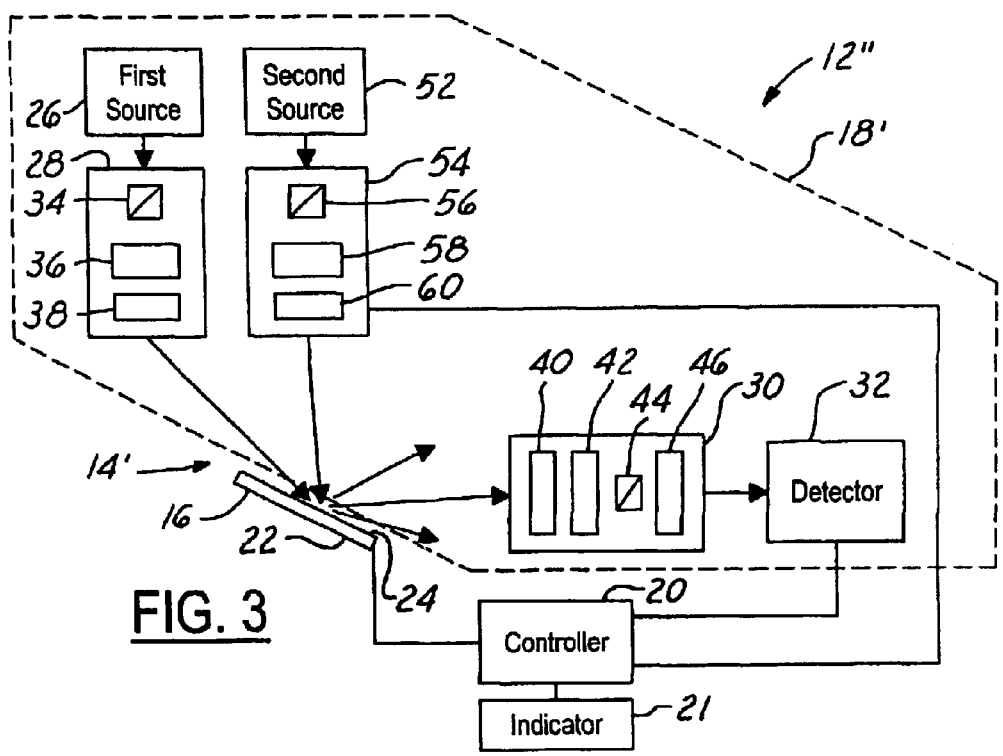
FIG. 3 is a block diagrammatic view of a hydrogen detection and sensor evaluation system having dual sources in accordance with another embodiment of the present invention.

Referring now to FIG. 3, a block diagrammatic view of a hydrogen detection and sensor evaluation system 12" having hydrogen detection system 14' in accordance with another embodiment of the present invention is shown. A surface spectroscopic system 18' includes the first source 26 and the first input device 28 that are used to transmit a fixed frequency and a second source 52 and a second input device 54 that are used to transmit a varied frequency. The first source 26, the second source 52, the first input device 28, and the second input device 54 may be included in a single unit or may be separate as shown.

The second input device 54 includes a second polarizer 56, a second amplitude adjuster 58, and a second frequency adjuster 58, which are similar to the first polarizer 34, the first amplitude adjuster 36, and the first frequency adjuster 38. The controller 20 is coupled to the second frequency adjuster 58 and varies frequency output of the second input device 54, which is explained in further detail below.

Figure 4:
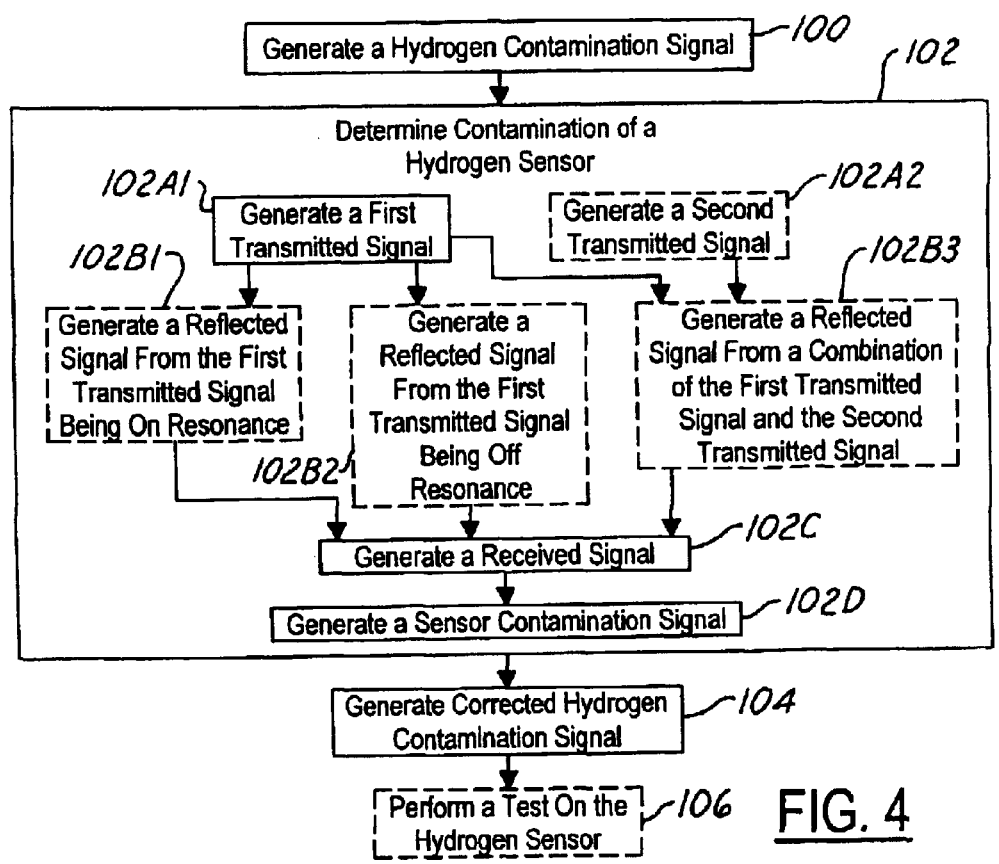
FIG. 4 is a logic flow diagram illustrating a method of detecting hydrogen and evaluating a hydrogen sensor in accordance with an embodiment of the present invention.

Referring now to FIG. 4, a logic flow diagram illustrating methods of detecting hydrogen and evaluating a hydrogen sensor in accordance with an embodiment of the present invention is shown.

In step 100, the hydrogen sensor 16 detects contamination in the reaction member 22 and generates a hydrogen contamination signal. The detected contamination may be due to hydrogen or other known elements or compounds impacting the impact surface 24 and reacting with the reaction member 22.

In step 102, contamination of the hydrogen sensor 16 is determined, which may include species identification and contamination level of the species.

In step 102A1, the first source 26 generates a first transmitted signal.

In step 102A2, the second source 52 may genetate a second transmitted signal.

In step 102B, the first source 26 adjusts and directs the first transmitted signal to impede upon and reflect from at least a portion of said hydrogen sensor 16 and form a reflected signal. In one embodiment of the present invention the first transmitted signal is transmitted having a first frequency harmonic and the reflected signal has a second frequency harmonic approximately equal to twice that of the first frequency. The first source 26 when adjusting the first transmitted signal selects a first set of desired fixed frequencies, which may be resonant with or non-resonant with hydrogen or with a hydrogen-palladium bond.

In step 102B1, non-resonant frequencies are selected. When the hydrogen sensor 16 is contaminated with hydrogen relatively little change between the transmitted signal and the reflected signal exists since the selected frequencies are off resonance. When the hydrogen sensor 16 is contaminated with elements other than hydrogen then a noticeable amplitude difference exists between the transmitted signal and the reflected signal. The amplitude may increase or decrease depending upon the species of contamination.

In step 102B2, resonant frequencies are selected. When the hydrogen sensor 16 is contaminated with hydrogen, a significant increase in amplitude exists between the transmitted signal and the reflected signal. When the hydrogen sensor 16 is contaminated with elements other than hydrogen, there is still a change in amplitude between the transmitted signal and the reflected signal but the change is significantly less than the change due to hydrogen contamination. In a sample embodiment of the present invention changes in hydrogen based resonant frequencies is approximately ten times greater than changes in non-resonant frequencies.

In step 102B3, the second input device 54 adjusts and directs the second transmitted signal to impede upon and reflect from the impact surface 24. The second source 52 when adjusting the second transmitted signal selects a second set of frequencies within a frequency range. The frequency range includes resonant frequencies, so that the second input device 54 is able to vary the selected frequencies on and off resonance with hydrogen or with a hydrogen-palladium bond. At least a portion of the first transmitted signal and at least a portion of the second transmitted signal upon reflecting from the impact surface 24 are combined to form the reflected signal having the first set of frequencies and the second set of frequencies.

The second transmitted signal is varied on and off resonance. When the hydrogen sensor 16 is contaminated with hydrogen the amplitude of the reflected signal is larger when the second transmitted signal is on resonance than when off resonance. When the hydrogen sensor 16 is contaminated with elements other than hydrogen there is relatively no change in amplitude of the reflected signal.

In step 102C, the output device 30 receives desired frequencies of the reflected signal and generates a received signal.

In step 102D, the detector 32 generates a sensor contamination signal in response to the received signal. Using one of the above techniques, the sensor contamination signal may include information such as whether hydrogen has been identified and an approximate contamination level of hydrogen in the reaction member 22. As with species identification, contamination level may also correspond with amplitude level of the reflected signal.

In step 104, the controller 20 compares the hydrogen contamination signal to the sensor contamination signal and generates a corrected hydrogen contamination signal and indicates as to whether the hydrogen sensor 16 is performing appropriately, via indicator 21. The hydrogen contamination signal signifies whether the hydrogen sensor 16 is contaminated, where as the surface spectroscopic system 18 determines whether the contamination is hydrogen and verifies contamination level of the hydrogen. The controller 20 monitors performance and efficiency of any regeneration process of the hydrogen sensor 16 and determines whether the sensor 16 needs to be recalibrated, repaired, or replaced. Regeneration refers to any chemical or physical process, which allows the sensor 16 to return to its initial physical state. Microchemical reactions, microcracking or microcrazing in the sensor 16 can lead to a slow long-term drift in the initial state of the sensor 16, which can reduce the possibility of the sensor 16 from returning to its initial condition, even in the relatively benign environment of cycling the sensor 16. When the changes in the sensor 16 lead to a signal offset, initial conditions are used as a means of internal calibration. When the changes are such that dynamic range of the sensor 16 is reduced, then repair or replacement may be desired.

In step 106, the hydrogen sensor 16 may be repaired, recalibrated, or replaced.

The above-described steps in the above methods are meant to be an illustrative example, the steps may be performed sequentially, synchronously, continuously, or in a different order depending upon the application.

The present invention provides a hydrogen detection and sensor evaluation system that is relatively simple and inexpensive to implement. The present invention is accurate in identifying hydrogen contamination and relatively quick in detecting hydrogen leaks.

The above-described apparatus and method, to one skilled in the art, is capable of being adapted for various applications and systems known in the art. The above-described invention can also be varied without deviating from the true scope of the invention.

What is claimed is:

1. A hydrogen detection system comprising:
   a hydrogen sensor detecting contamination of a reaction member and generating a hydrogen contamination signal;
   a surface spectroscopic system operational in conjunction with said hydrogen sensor and determining contamination of said hydrogen sensor and generating a sensor contamination signal; and a controller electrically coupled to the hydrogen sensor and the surface spectroscopic system and comparing said hydrogen contamination signal to said sensor contamination signal and generating a corrected hydrogen contamination signal.

2. A system as in claim 1 wherein said surface spectroscopic system in determining, contamination of said hydrogen sensor determines species identity of said contamination.

3. A system as in claim 1 wherein said surface spectroscopic system in determining contamination of said hydrogen sensor determines concentration level of said contamination.

4. A system as in claim 1 wherein said hydrogen sensor is formed at least partially of palladium.

5. A system as in claim 1 wherein said surface spectroscopic system comprises:

a first source generating a first transmitted signal;

a first input device adjusting and directing said first transmitted signal to impede upon and reflect from at least a portion of said hydrogen sensor and form a reflected signal;

an output device receiving at least a portion of said reflected signal and generating a received signal; and a detector generating said sensor contamination signal in response to said received signal.

6. A system as in claim 5 wherein said sensor contamination signal is generated in response to amplitude of said received signal.

7. A system as in claim 5 wherein said input device and said output device are configured in response to resonant frequencies of said hydrogen sensor.

8. A system as in claim 5 wherein said input device and said output device are configured in response to non-resonant frequencies of said hydrogen sensor.

9. A system as in claim 5 wherein said input device and said output device are configured in response to resonant frequencies of a contaminated surface of said hydrogen sensor.

10. A system as in claim 5 wherein said input device and said output device are configured in response to non-resonant frequencies of a contaminated surface of said hydrogen sensor.

11. A system as in claim 5 wherein said input device and said output device are configured in response to a resonant frequency of hydrogen.

12. A system as in claim 5 wherein said input device and said output device are configured in response to a resonant frequency of a hydrogen-palladium bond.

13. A system as in claim 5 further comprising:

a second source generating a second transmitted signal; and a second input device adjusting and directing said second transmitted signal to impede upon and reflect from at least a portion of said hydrogen sensor;

said output device receiving at least a portion of said reflected signal generated from a combination of at least a portion of said first transmitted signal and at least a portion of said second transmitted signal reflecting off said hydrogen sensor.

14. A system as in claim 13 wherein said first input device selects a portion of said first transmitted signal having a fixed frequency and said second input device selects a portion of said second transmitted signal within a frequency range containing a resonance frequency of said hydrogen sensor.

15. A system as in claim 14 wherein selects said second transmitted signal said second input device selects a portion of said second transmitted signal within a frequency range containing a resonance frequency of a contaminated surface of said hydrogen sensor.

16. A system as in claim 13 wherein said sensor contamination signal is generated in response to changes in said reflected signal when frequency of said second transmitted signal is varied.

17. A system as in claim 1 wherein said surface spectroscopic system is a SurfS diagnostic system.

18. A method of detecting hydrogen within a hydrogen detection system comprising:

detecting contamination of a reaction member via a hydrogen sensor and generating a hydrogen contamination signal;

determining contamination of said hydrogen sensor comprising;

generating at least one transmitted signal;

adjusting and directing said at least one first transmitted signal to impede upon and reflect from at least a portion of said hydrogen sensor and form a reflected signal;

receiving at least a portion of said reflected signal and generating a received signal; and generating a sensor contamination signal in response to said received signal; and comparing said hydrogen contamination signal to said sensor contamination signal and generating a corrected hydrogen contamination signal.

19. A method of evaluating a hydrogen sensor of a hydrogen-fueled vehicle comprising:

detecting contamination of a reaction member via a hydrogen sensor and generating a hydrogen contamination signal;

determining contamination of said hydrogen sensor comprising;

generating at least one transmitted signal;

adjusting and directing said at least one first transmitted signal to impede upon and reflect from at least a portion of said hydrogen sensor and form a reflected signal;

receiving at least a portion of said reflected signal and generating a received signal; and generating a sensor contamination signal in response to said received signal;

comparing said hydrogen contamination signal to said sensor contamination signal and generating a corrected hydrogen contamination signal; and performing at least one action in response to said corrected hydrogen contamination signal selected from at least one of replacing said hydrogen sensor, recalibrating said hydrogen sensor, generating recalibration information, repairing said hydrogen sensor, and indicating efficiency of any regeneration process.

20. A hydrogen detection system comprising:

a hydrogen sensor detecting contamination of a reaction member and generating a hydrogen contamination signal;

a surface spectroscopic system operational in conjunction with said hydrogen sensor and determining contamination of said hydrogen sensor, said surface spectroscopic system comprising;

a first source generating a first transmitted signal;

a first input device adjusting and directing said first transmitted signal to impede upon and reflect from at least a portion of said hydrogen sensor and form a reflected signal;

an output device receiving at least a portion of said reflected signal and generating a received signal; and a detector generating a sensor contamination signal in response to said received signal; and a controller electrically coupled to the hydrogen sensor and the surface spectroscopic system and comparing said hydrogen contamination signal to said sensor contamination signal and generating a corrected hydrogen contamination signal.

* * * * *